(12) United States Patent
O'Connor et al.

(10) Patent No.: US 11,842,801 B2
(45) Date of Patent: Dec. 12, 2023

(54) SYSTEMS AND METHODS FOR GUIDING TRAVERSAL THROUGH LOGIC SERIES FOR EVENT CHAINS

(71) Applicant: Cohere Health, Inc., Boston, MA (US)

(72) Inventors: Niall O'Connor, Somerville, MA (US); Matt Murphy, Boston, MA (US)

(73) Assignee: Cohere Health, Inc., Boston, MA (US)

( * ) Notice: Subject to any disclaimer, the term of this patent is extended or adjusted under 35 U.S.C. 154(b) by 0 days.

(21) Appl. No.: 17/705,965

(22) Filed: Mar. 28, 2022

(65) Prior Publication Data

US 2022/0319682 A1   Oct. 6, 2022

Related U.S. Application Data

(60) Provisional application No. 63/166,426, filed on Mar. 26, 2021.

(51) Int. Cl.
*G16H 40/20* (2018.01)
*G06Q 10/109* (2023.01)
*G16H 10/60* (2018.01)

(52) U.S. Cl.
CPC ........... *G16H 40/20* (2018.01); *G06Q 10/109* (2013.01); *G16H 10/60* (2018.01)

(58) Field of Classification Search
CPC .......... G16H 40/20; G16H 10/60; G16H 70/20
See application file for complete search history.

(56) References Cited

U.S. PATENT DOCUMENTS

| | | | |
|---|---|---|---|
| 2002/0019749 A1* | 2/2002 | Becker | G06Q 40/08 705/2 |
| 2020/0082941 A1* | 3/2020 | Wang | G16H 50/20 |
| 2021/0012898 A1* | 1/2021 | Santos | G16H 70/20 |

FOREIGN PATENT DOCUMENTS

WO    WO-2020074191 A1 *  4/2020  ......... G06F 16/9024

* cited by examiner

*Primary Examiner* — Mark Holcomb
(74) *Attorney, Agent, or Firm* — Mughal Gaudry & Franklin PC

(57) ABSTRACT

The present embodiments relate to generation of event chains and processing of events using the event chains. According to certain embodiments, the embodiments relate to generation of event chains and processing of events using the event chains. According to other embodiments, the embodiments relate to identifying a sub-population of subjects for providing a modified request-processing technique. According to other embodiments, the embodiments relate to auto-completion of event chains for triggering auto-processing of events.

18 Claims, 6 Drawing Sheets

Event Chain 1        Event Chain 2

100

SYSTEMS AND METHODS FOR GUIDING TRAVERSAL THROUGH LOGIC SERIES FOR EVENT CHAINS

CROSS-REFERENCE TO RELATED APPLICATION(S)

This application claims priority to U.S. Provisional Patent Application No. 63/166,426, titled "SYSTEMS AND METHODS FOR GUIDING TRAVERSAL THROUGH LOGIC SERIES FOR EVENT CHAINS," and filed Mar. 26, 2021, the entirety of which is incorporated by reference herein.

BACKGROUND

A subject can have one or more conditions. The condition can be a medical condition (e.g., knee pain, dental cavity), and various actions can be taken in response the condition. For example, one or more events (e.g., laboratory scans, procedures, therapies) can be performed in an order to alleviate or mitigate the condition.

In many instances, approval of each event can be requested prior to performance of the event. For example, this can include providing a request for approval of an event with an event code specifying the event to an authorizing entity for approval and receiving either an approval or rejection of the event. Such a process can be inefficient, as each event of a series of events may need to be approved prior to performance of each event, and a delay may exist between requesting approval of each event and receipt of the approval of the event.

SUMMARY

Some embodiments of the present disclosure are directed to, among other things, generation of event chains and processing of events using the event chains. According to certain embodiments, a method for generation of event chains and processing of events using the event chains is provided. The method can include retrieving subject data relating to a set of subjects. The method can also include generating a series of event chains. Each of the series of event chains can be derived based on a subset of the subject data relating to the set of subjects. Each event chain can comprise multiple events relating to each subset of subject data. Each event of the multiple events can be associated with a timestamp for performance of the event.

The method can also include identifying a first event chain of the series of event chains that corresponds to a first subset of subject data. The method can also include obtaining a request for approval of a first event, the first event including a timestamp for the first event. The method can also include responsive to determining that the first event and the timestamp for the first event corresponds to the first event chain, providing an acceptance message indicating an acceptance of the first event.

According to certain embodiments, a method for identifying a sub-population of subjects for providing a modified request-processing technique is provided. The method can include generating a baseline event chain that corresponds to a subset of subject data. The method can also include identifying a set of subjects that correspond with the subset of subject data. The method can also include tracking, for each subject of the set of subjects, each event representing an action performed in association with the subject.

The method can also include generating, for each subject of the set of subjects, an event chain based on the tracked events. The method can also include detecting a subset of the set of subjects for which a particular departure between the event chains associated with subjects in the subset and the baseline event chain is observed. The method can also include defining a series of common elements for the subset of the set of subjects. The method can also include generating a unique event chain based on the series of common elements, the unique event chain associated with the subset of subject data. The method can also include obtaining a request for approval of a first event associated with a particular subject. The method can also include, responsive to determining that the first event corresponds to any event in the baseline event chain or the unique event chain, providing an acceptance message indicating an acceptance of the first event.

According to certain embodiments, a method for auto-completion of event chains for triggering auto-processing of events is provided. The method can include receiving subject data relating to a subject via an interface executing on a computing device. The method can also include identifying a first processing flow that corresponds with a subset of the subject data relating to the subject. The method can also include processing the first processing flow using the subset of the subject data to identify a series of events corresponding with the first processing flow.

The method can also include updating the interface to display the series of events corresponding with the first processing flow. The method can also include detecting a selection of a first event to be performed to the subject. The method can also include, responsive to determining that the first event is included in the series of events, displaying an acceptance message on the interface identifying the first event as an accepted event to be performed to the subject.

In some embodiments, a system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions that have been employed are used as terms of description and not of limitation, and there is no intention in the use of such terms and expressions of excluding any equivalents of the features shown and described or portions thereof. It is recognized, however, that various modifications are possible within the scope of the systems and methods claimed. Thus, it should be understood that, although the present system and methods have been specifically disclosed by examples and optional features, modification and variation of the concepts herein disclosed should be recognized by those skilled in the art, and that such modifications and variations are considered to be within the scope of the systems and methods as defined by the appended claims.

This summary is not intended to identify key or essential features of the claimed subject matter, nor is it intended to be used in isolation to determine the scope of the claimed subject matter. These illustrative examples are mentioned not to limit or define the disclosure, but to provide examples to aid understanding thereof. Additional embodiments and examples are discussed in the Detailed Description, and further description is provided there. The subject matter should be understood by reference to appropriate portions of the entire specification of this disclosure, any or all drawings, and each claim.

The foregoing, together with other features and embodiments will become more apparent upon referring to the following specification, claims, and accompanying drawings.

BRIEF DESCRIPTION OF THE FIGURES

Features, embodiments, and advantages of the present disclosure are better understood when the following Detailed Description is read with reference to the following figures.

DETAILED DESCRIPTION

Figure 1:
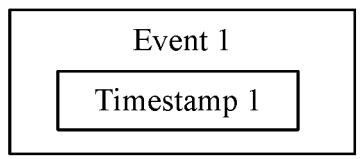
FIG. 1 is a block diagram illustrating multiple event chains.
Figure 1:
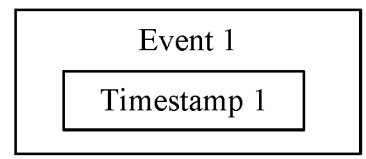
Figure 1:
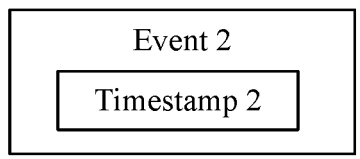
Figure 1:
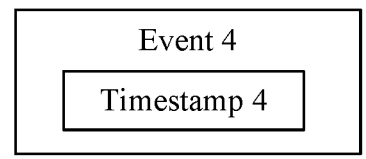
Figure 1:
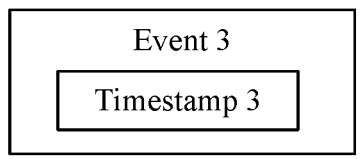
Figure 1:
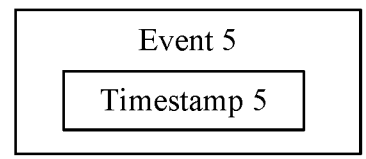
Figure 1:
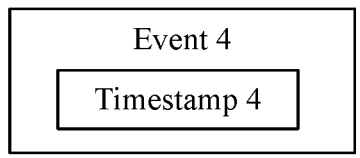
Figure 1:
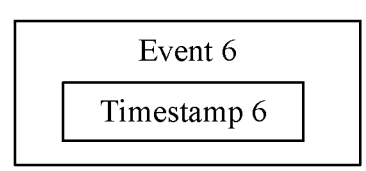
Figure 1:
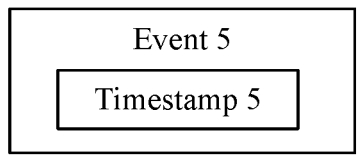
Figure 1:
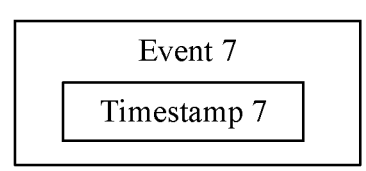

The term "subject data" can include data that relates to a subject. For example, subject data can specify a condition (e.g., knee pain, a dental cavity) relating to the subject or a historical medical characteristic relating to the subject. The condition may include a medical condition, a medical disease, or a symptom. Subject data can also specify other medical record data or demographic data relating to the subject that can be used in generation and processing of event chains as recited herein. A subset of subject data can include a particular condition specified in the subject data.

The term "event" can include an action to be performed with respect to a subject. The action may include (for example) holding an appointment (e.g., with a care provider, such as a doctor, nurse, therapist, skilled nursing facility care provider, home health agency provider, outpatient physical therapy provider, outpatient rehabilitation facilitation provider, end-stage renal disease facility provider, hospice provider, laboratory entity, surgeon, supplier, etc.), performing a surgery, collecting data of a particular type (e.g., a medical image), performing a particular assay (e.g., to analyze a blood sample), providing a prescription, or providing a therapy session. For example, an event can include performance of a scan of a portion of the subject, a procedure (e.g., surgical procedure), a therapy (e.g., physical therapy), or another action associated with the subject.

The term "event chain" can specify one or more associated events. For example, the event chain can specify a series of events to perform with respect to the subject. As an illustrative example, an event chain can include three events, where a first event includes a preliminary scan, a second event includes a procedure, and a third event includes post-procedure therapy. Each event can include a timestamp indicating a time to perform each event with respect to the other events in the event chain. For instance, in the above example, a timestamp for the second event can indicate that the second event is to be performed prior to the third event but after the first event. As another example, a timestamp may indicate how long (e.g., in terms of an absolute time or a time period) a given event is separated from a previous event. To illustrate, a proposed given event (e.g., surgery) may be associated with a time that is within 3 months from a time at which an imaging process was performed.

The event chain can identify a series of events and can be used for approval of an event. In some embodiments, the event chain can specify a series of approved events for a specified condition. For example, an event included in the event chain can be approved responsive to determining that the event corresponds with the event chain. In other embodiments, the event chain can include a series of events that have been performed to the subject. Determining that the event corresponds with the event chain can include identifying that the requested event matches an event included in the event chain and that the requested event corresponds with a timestamp associated with the event in the event chain.

An event chain or a series of events may identify a default series of events, which may identify events that are, by default, approved for treatment of a given condition (e.g., so long as the events are performed in an order and/or time series as indicated in the default series of events and/or so long as the subject data conforms with corresponding condition data). The default series of events may identify a set of events, where each sequential pair of events may be associated with a time period (e.g., associated with a minimum time-duration interval and/or maximum time-duration interval) and/or event-chain progression condition (e.g., which is to be satisfied to result in the series of events advancing to a next event).

The present embodiments relate to guiding traversal through logic series for event chains. In some embodiments, a method for machine-learning processing of event chains to detect influential events is disclosed. Each claim code can represent a treatment or service. Thus, an event chain can be constructed for each subject that identifies a sequence of treatments or services. Each event may also be associated with a timestamp. A set of event chains (associated with multiple subjects) can be analyzed to detect events for which occurrence of the event was predictive of (for example) a final state of the subject, a length of the event chain (e.g., quantity of treatments), a time period of the event chain (e.g., total treatment time), and/or a severity (e.g., whether high-risk treatments were eventually provided).

In some embodiments, methods for using a clustering technique to identify sub populations for which a modified request-processing approach is to be provided are disclosed. Each subject of a set of subjects (e.g., who have a particular condition) can be associated with a data set that represents (for example) demographics, treatment history, genetic data, etc. In some instances, the data set is structured to indicate relative timing of multiple treatments. A clustering technique can be performed. The clusters may be analyzed to detect (for example) a particular sub-population that did not receive a particular type of treatment or that included data points indicating particularly good or particularly poor prognosis. For example, it may be discovered that a sub-population with a particular mutation or with a particular co-morbidity frequently does not receive a standard treatment. A process flow for processing requests may then be changed for that sub-population.

In some embodiments, methods for auto-completion representative of event chains for triggering auto-processing are disclosed. A condition or symptom relating to a subject may be received via an interface or identified based on data from a record of the subject. Information about the subject (e.g., including demographics and/or treatment history) may be received via the interface, retrieved from storage, or retrieved from another source. This information can be used to identify a processing flow (e.g., decision tree) that pertains to the subject. Based on the processing flow and subject data, a computing system can identify a set of events that comply with a decision tree used to determine responses to requests. Some of the events may correspond to multiple circumstances and/or characteristics. An interface may be presented that indicates which events comply with the decision tree. An event may be one that would comply at any time, if representative of an occurrence in the recent path, if representative of an occurrence in the recent future, or if representative of an occurrence in the far future. In some instances, a chain of events that would comply with the decision tree are identified (e.g., 3-5 physical therapy (PT) sessions and then surgery). The interface may further accept input that indicates that such an event actually occurred and that payment is requested.

In some embodiments, methods for exception handling based on past adherence to event-chain constraints are disclosed. For a given medical condition, a set of event-chain constraints can be defined that indicate which types of treatments/services are authorized for reimbursement and in which circumstances. Each of a set of providers may submit requests for payment, and each request can be assessed based on applicable event-chain constraints (e.g., that apply to a subject's condition). An analysis can be performed to identify providers who have high adherence to the applicable constraints, and the constraints can then be adjusted. For example, the constraints may be gradually weakened, one or more constraints may be removed, and/or the constraints may be entirely discarded for a particular period of time or number of requests.

In some embodiments, methods providing a centralized portal for processing requests ultimately handled by multiple entities is disclosed. Each provider plan can have their own set of rules to use to determine whether to approve or deny a payment request. Here, a centralized system can be configured with a dynamic rules base that tracks the rules of each plan. The centralized system can also be authorized to access a system of each provider (e.g., by logging in as a provider or based on authorization from the provider plan). The centralized system may transform and distill a rule set from a provider to a more comprehensible and focused set of questions or information that can be availed to a provider in an interface. Further, the centralized system may receive information from a provider and transform the information into a pre-authorization and/or payment request that is then transmitted to the provider. This approach can be highly useful to providers who accept multiple insurances, as it provides a single front door.

While some examples in the present embodiments relate to treatments or services for medical conditions relating to one or more individuals, the present embodiments are not limited to such examples. For example, the present embodiments can specify an event chain for mitigating a condition identified in a computer or computing network. For instance, a condition can include an issue related to a computer, such as a malware or a cybersecurity breach of one or more computers in a computing environment. In this example, an event chain can be identified for mitigating the issue, such as an event chain specifying actions relating to (1) identifying all impacted computing instances, (2) isolating the impacted computing instances from the computing network, and (3) migrating a workload from the impacted computing instances to another computing instance. Events can then be performed by a provider (e.g., an administrator of the computing network, a software program on the computing network) according to the specified event chain.

The following examples are provided to introduce certain embodiments. In the following description, for the purposes of explanation, specific details are set forth in order to provide a thorough understanding of examples of the disclosure. However, it will be apparent that various examples may be practiced without these specific details. For example, devices, systems, structures, assemblies, methods, and other components may be shown as components in block diagram form in order not to obscure the examples in unnecessary detail. In other instances, well-known devices, processes, systems, structures, and techniques may be shown without necessary detail in order to avoid obscuring the examples. The figures and description are not intended to be restrictive. The terms and expressions that have been employed in this disclosure are used as terms of description and not of limitation, and there is no intention in the use of such terms and expressions of excluding any equivalents of the features shown and described or portions thereof. The word "example" is used herein to mean "serving as an example, instance, or illustration." Any embodiment or design described herein as an "example" is not necessarily to be construed as preferred or advantageous over other embodiments or designs.

I. Chain Generation and Approval of Events Using Event Chains

In some embodiments, methods for generating a series of event chains, identifying an event chain that corresponds to a subset of subject data relating to a subject, and providing an acceptance message accepting a requested event based on determining that the requested event corresponds with an event in the event chain are provided.

Information relating to a group of subjects can be obtained and a series of event chains can be generated based on a subset of subject data. For example, for a subset of subject data (e.g., a dental cavity), an event chain can be generated that includes performing the events of: conducting an X-ray and performing a procedure to fill the cavity. In this example, an event chain can be generated with events corresponding to the X-ray and the procedure. This processed can be performed to generate multiple event chains relating to various conditions.

A request for approval of a first event can be obtained. An event chain that corresponds to the first event can be retrieved. For example, an event chain can be identified that corresponds with a specified condition. The event chain can be processed to determine whether the first event corresponds with any event in the event chain. This can include identifying that the first event is included in the event chain and determining that a timestamp of the first event corresponds to a timestamp of an event in the first event chain.

Responsive to determining that the first event and the timestamp for the first event corresponds to the first event chain, an acceptance message can be provided that indicates an acceptance of the first event.

FIG. 1 is a block diagram 100 illustrating multiple event chains. As noted above, an event chain can include a series of associated events. The event chain can specify an order in which to execute the events, indicated by a timestamp associated with each event.

As an illustrative example, a first event chain can include events 1-5 and corresponding timestamps 1-5. Each event can indicate an action to be performed with respect to the subject. For example, in event chain 1, events 1 and 2 can include tests to be performed, event 3 can include a procedure, and events 4 and 5 can include various therapies to be performed.

In some embodiments, a second event chain can differ from the first event chain. The second event chain can represent a secondary order to alleviate a specified condition or another way to alleviate a condition if other conditions exist for a subject. For example, the second event chain can include event 1 that is similar to an event in event chain 1 but can exclude events 2 and 3 in event chain 1. As an illustrative example, the second event chain can remove a specific test and a procedure and include events 4 and 5 that include various therapies and events 6 and 7 that include other therapies.

Figure 2:
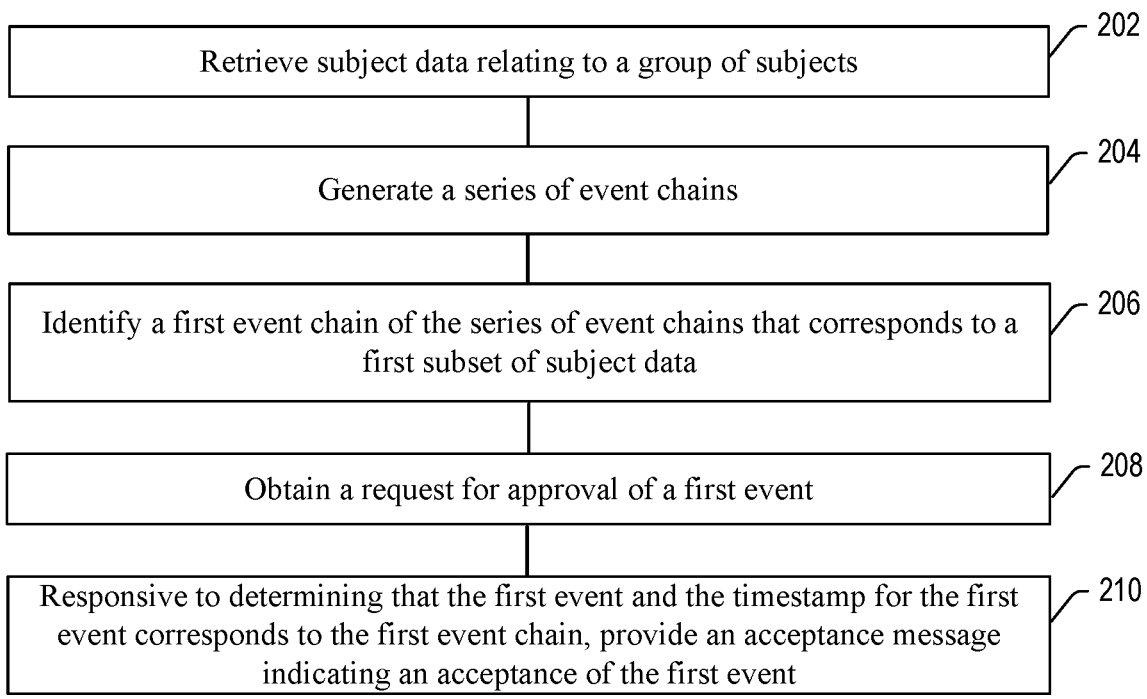
FIG. 2 is a flow process illustrating a method for generating event chains and approving an event using the event chains.

FIG. 2 is a flow process 200 illustrating a method for generating event chains and approving an event using the event chains. At block 202, the method can include retrieving subject data relating to a set of subjects. The subject data relating to the set of subjects can include various information relating to the set of subjects (e.g., conditions relating to the set of subjects, demographic information, events performed to the set of subjects, a result of the events performed to the set of subjects). For example, the subject data can specify a specific condition and a series of events performed in response to the specific condition. In some embodiments, the subject data can be retrieved via an interface executing on a computing device. For example, an interface can allow for interaction with a user and/or external computing devices to obtain various subject data.

At block 204, the method can include generating a series of event chains. Each of the series of event chains can be derived based on a subset of the subject data relating to the set of subjects. Each event chain can include multiple events relating to each subset of subject data. In some embodiments, each event in the event chain can correspond to an event code identifying each event.

Each event of the multiple events can also be associated with a timestamp for performance of the event. The timestamp can indicate a time to perform each event relative to another event in the event chain.

At block 206, the method can include identifying a first event chain of the series of event chains that corresponds to a first subset of subject data. For example, a first event chain can be identified that corresponds to a specific condition identified in the first subset of subject data.

At block 208, the method can include obtaining a request for approval of a first event. The first event can include a timestamp for the first event. For example, prior to performance of a first event, an approval may be requested to approve performance of the first event as corresponding with the event chain.

At block 210, the method can include providing an acceptance message indicating an acceptance of the first event responsive to determining that the first event and the timestamp for the first event corresponds to the first event chain. In some embodiments, determining that the first event and the timestamp for the first event corresponds to the first event chain includes determining that a first event code associated with the first event corresponds with an event code of an event included in the first event chain and determining that the timestamp for the first event corresponds to a timestamp of the event included in the first event chain.

In some embodiments, responsive to determining that the first event and the timestamp for the first event does not correspond to any event in the first event chain, a rejection message can be provided indicating a rejection of the first event.

As noted above, an event can be approved responsive to the event corresponding with an identified event chain. For instance, an event (e.g., a request to provide physical therapy) can be specified for a condition (e.g., a condition relating to a knee injury) to be performed to remediate the condition. Further, the provider can provide a request for approval of the event and obtain a notification of whether the event corresponds with the event chain and is approved. In the event is rejected, a recommended event that corresponds with the event chain can be provided to the provider. As an example, for a condition (e.g., knee pain), an event chain can include events relating to (1) performing an X-ray or MRI, and (2) performing physical therapy sessions. In this example, if the provider provides a request for an event that does not correspond with this event chain (e.g., a request to perform physical therapy while no X-ray or MRI was performed), a notification rejecting the event can include the event that corresponds with the event chain (e.g., the event for performing an X-ray or MRI). This can allow for the provider to view events that correspond to an event chain and adapt subsequent proposed events to correspond with the event chains derived herein.

II. Identifying a Sub-Population for Providing a Modified Request-Processing Technique In some embodiments, methods for identifying a sub-population of subjects associated with events that differ from a baseline event chain and adding the unique event chain for event processing are provided. For example, a baseline event chain can include a series of events that correspond to a subset of subject data (e.g., a specified condition for a set of subjects). A series of events can be tracked relating to a set of subjects and a number of event chains can be generated that differ from the baseline event chain. For example, if a baseline event chain relates to performing an X-ray and then performing a cavity fill procedure for a dental cavity, a new event chain identified can include only performing the cavity fill procedure without prior performance of the X-ray.

A series of common elements between the baseline event chain and the new event chains can be identified for the subset of the set of subjects. For example, a common result of performance of the events or a number of common events in a specified order can be identified to generate a unique event chain. The unique event chain can be associated with the baseline event chain and the subset of subject data for subsequent processing. For example, a request for approval of a first event for a subject can be obtained. After determining that the first event corresponds to any event in the baseline event chain or the unique event chain, an acceptance message can be provided indicating an acceptance of the first event.

Figure 3:
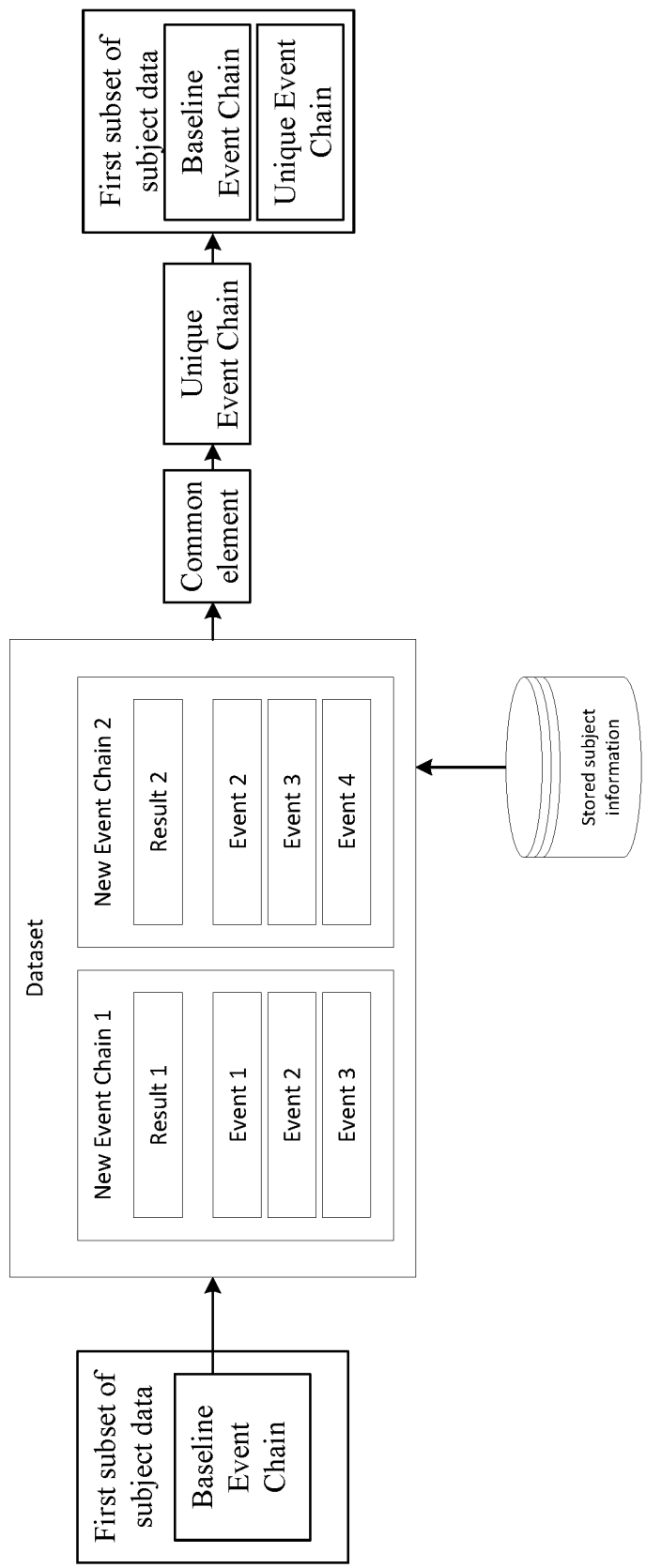
FIG. 3 illustrates a system for identifying a sub-population of subjects for providing a modified request-processing technique.

FIG. 3 illustrates a system 300 for identifying a sub-population of subjects for providing a modified request-processing technique. As shown in FIG. 3, a first subset of subject data can be associated with a baseline event chain. For example, a specified condition (e.g., knee pain) can relate to a baseline event chain comprising the events of performing an X-ray and then performing a series of physical training actions.

The baseline event chain and stored subject data can be utilized in generating a dataset. The stored subject data can include data relating to a group of subjects, such as conditions relating to the subjects, events performed to the subjects, historical event data, etc.

The dataset can provide a set of data relating to the subjects. For example, a dataset can track events relating to each subject and generate a number of event chains relating to each subject. As shown in FIG. 3, a number of new event chains can be generated based on the subject data relating to each subject in a set of subjects. Any of the new event chains can specify differing events that deviate from the baseline event. For example, a first new event chain can include a first series of events, while a second new event chain can include a second series of events that differ from the baseline event chain. In some embodiments, one or more clusters can be identified in the dataset for subsequent processing as described herein.

The new event chains and the baseline event chain can be processed to identify a number of common elements. The common elements can include similarities between the new event chains and the baseline event chain. The common elements can be used to generate a unique event chain. The unique event chain can be associated with the baseline event chain as being associated with the first subset of subject data.

Figure 4:
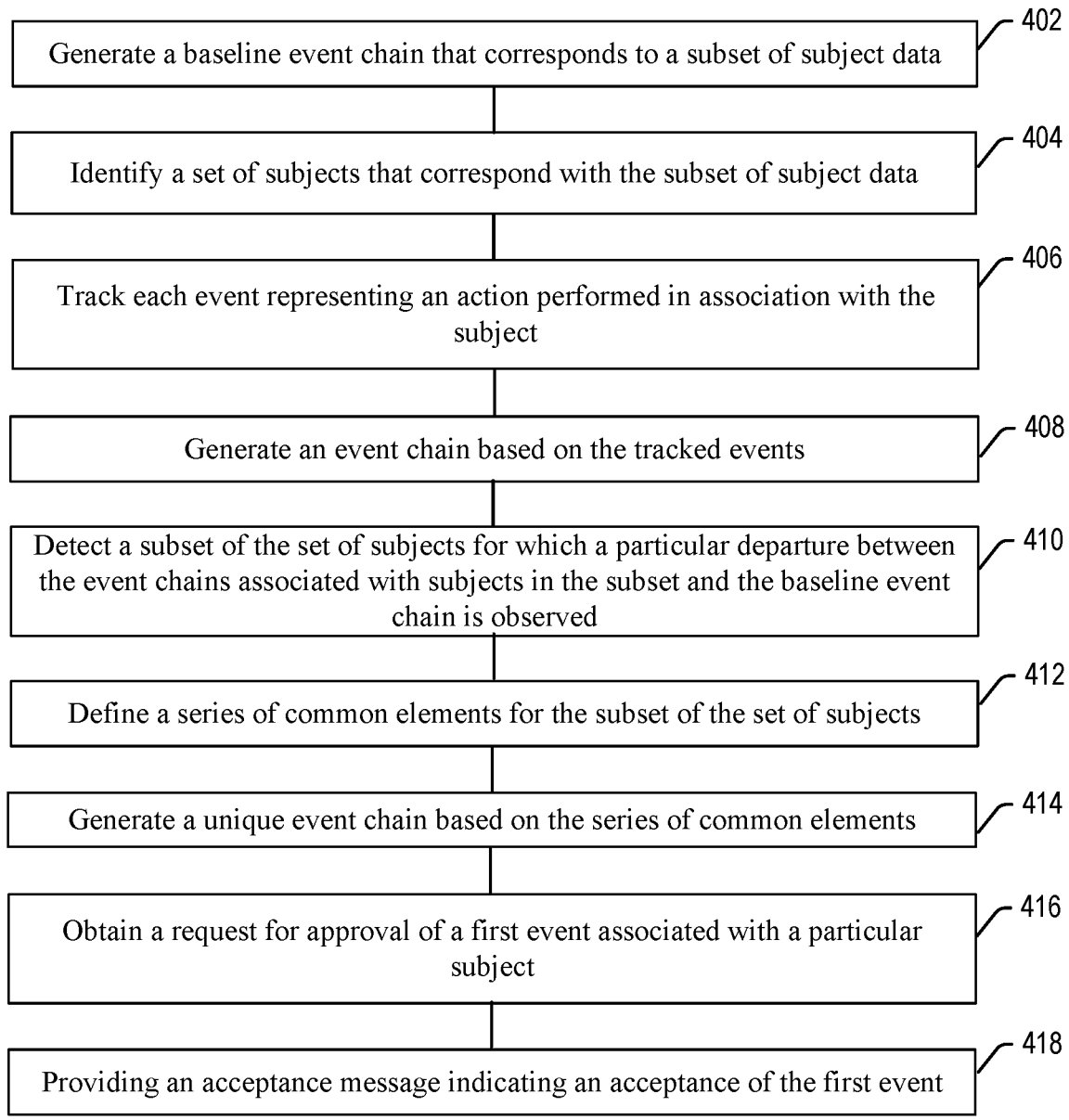
FIG. 4 is a block diagram of a method for identifying a sub-population of subjects for providing a modified request-processing technique.

FIG. 4 is a block diagram of a method 400 for identifying a sub-population of subjects for providing a modified request-processing technique. At block 402, the method can include generating a baseline event chain that corresponds to a subset of subject data. As noted above, the baseline event chain can include a series of events that can be performed relating to a subset of subject data for a group of subjects.

At block 404, the method can include identifying a set of subjects that correspond with the subset of subject data. This can include identifying a group of subjects with conditions that correspond to the baseline event chain. For example, if the baseline event chain relates to alleviating a dental cavity, a group of subjects that also had a dental cavity can be identified.

At block 406, the method can include tracking each event representing an action performed in association with the subject. Each subject of the set of subjects can have subject data processed to identify each event that relates to the subject. Other subject data can be identified, such as a number of events performed to each subject, a timestamp of performing each event, a result of performance of each event, etc.

At block 408, the method can include generating an event chain based on the tracked events for each subject of the set of subjects. Each event chain can be unique to each subject and can deviate from the baseline event chain.

At block 410, the method can include detecting a subset of the set of subjects for which a particular departure between the event chains associated with subjects in the subset and the baseline event chain is observed. This can include identifying one or more event chains that, for a similar condition as a condition relating to the baseline event chain, include a different order/number of events to alleviate the condition, for example. The event chains that deviate from the baseline event chain can be indicative of another event chain that can alleviate a condition for a sub-population of subjects.

In some embodiments, a dataset can be used for detecting the subset of the set of subjects for which a particular departure between the event chains associated with subjects in the subset and the baseline event chain is observed. The dataset can be indicative of a first result of a performance of the baseline event chain to the set of subjects and a second result of a performance of the unique event chain to the subset of the set of subjects. Further, the dataset can be processed to derive the series of common elements for the subset of the set of subjects, as described below.

In some embodiments, events provided by a provider can be compared with a baseline event chain as described herein. For example, for a condition relating to a dental cavity, a baseline event chain can include a first event to perform an x-ray and a second event to fill the cavity. Providers can provide events for approval that correspond with the baseline event chain. Further, a subset of events provided can be identified that depart from the baseline event chain. For example, for the same condition, a subset of events provided by providers can include only an identifying filling the cavity without the prior event of performing an x-ray. In some instances, the subset of providers providing events that deviate from the baseline event chain can be used to generate a new event chain for a specified condition as described herein. For example, an event chain of first performing a dental check-up and then filling a cavity may be repeatedly observed and may then be defined (e.g., after a sufficient number of observances across providers) as corresponding to an approved event chain (e.g., corresponding to detecting and filling a micro-cavity). Additionally or alternatively, the newly generated event chain(s) can be used to manage recommended events provided to providers as described above. For example, if a provider identifies one or more events that do not correspond with any of a set of pre-defined event chains, it can be determined whether the provided event corresponds with a newly generated event chain for a specific condition. If the provided event corresponds with a newly generated event chain, the event can be approved, and details of the event being approved can be provided to the provider. Further, in some instances, if an event is rejected, recommended events for both an identified event chain and a newly generated event chain for a specified condition can be provided to the provider to provide insights into events that are approved for the specified condition.

At block 412, the method can include defining a series of common elements for the subset of the set of subjects. The series of common elements can include a first result being within a threshold similarity to a second result as identified in the dataset. In some embodiments, the series of common elements can include a number of events that are included in the baseline event chain and also relate to the subset of the set of subjects.

At block 414, the method can include generating a unique event chain based on the series of common elements. The unique event chain can be associated with the subset of subject data. The unique event chain can specify a sub-population of the set of subjects that include a common set of events derived from the event chains created for each subject.

At block 416, the method can include obtaining a request for approval of a first event associated with a particular subject.

At block 418, the method can include providing an acceptance message indicating an acceptance of the first event. This can be performed responsive to determining that the first event corresponds to any event in the baseline event chain or the unique event chain.

In some embodiments, determining that the first event corresponds to any event in the baseline event chain or the unique event chain includes matching a received event code associated with the first event with an event code of the event included in the baseline event chain or the unique event chain and determining that a received timestamp for the first event corresponds to a timestamp of the event included in the baseline event chain or the unique event chain.

III. Auto-Completion of Event Chains Using Processing Flows

In some embodiments, methods for auto-completion of event chains for triggering auto-processing of events are provided. The present embodiments can provide efficient processing of incoming events and approval of events using a selected processing flow specific to subject data relating to a subject.

An interface executing on a computing device can obtain subject data relating to a subject. For example, this can include condition data, historical records, etc., relating to a subject. The interface can provide a menu (e.g., a drop down menu) for providing the subject data and, in many cases, subject data can be received from external computing devices.

A first processing flow can be identified that corresponds with the received subject information. Each processing flow can include a series of queries (e.g., a decision tree) that can be executed using the subject data. For example, a first processing flow that corresponds to the subject data (e.g., a condition associated with the subject) can be processed to identify a series of events. The series of events can include events that are approved to be performed to the subject.

The interface can be updated to display the series of events that correspond to the first processing flow. In response, the interface can obtain a selection of a first event to be performed. The system can determine whether the first event is included in the series of events. Responsive to determining that the first event is included in the series of events, an acceptance message on the interface can be displayed identifying the first event as an accepted event to be provided to the subject.

Figure 5:
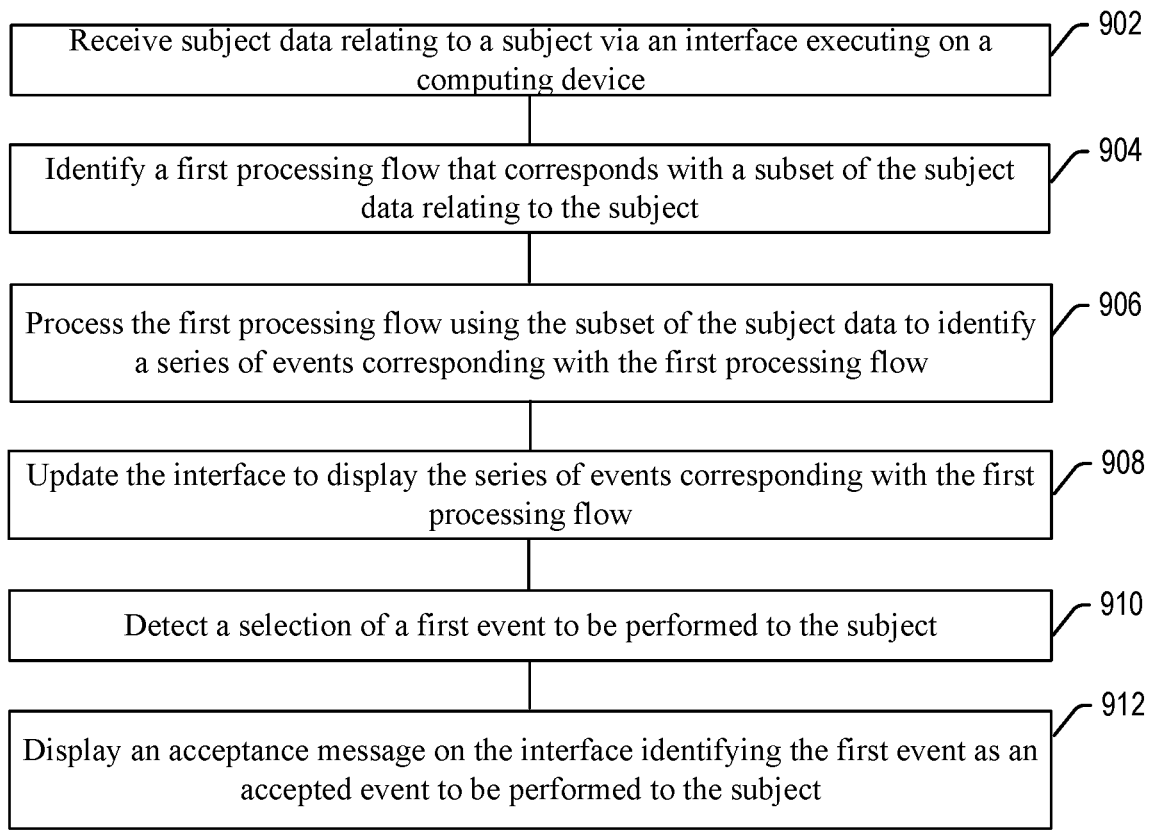
FIG. 5 is a block diagram of an example method for auto-completion of event chains for triggering auto-processing of events.

FIG. 5 is a block diagram of an example method 500 for auto-completion of event chains for triggering auto-processing of events. At block 502, the method can include receiving subject data relating to a subject via an interface executing on a computing device. For example, the subject data can specify a condition relating to a subject.

In some embodiments, the subset of the subject data can be received at the interface and/or from an external storage module. Further, the subset of the subject data can include an event history for the subject. This can include medical history for the subject, for example. In some instances, the additional subject data can be used to further specify the processing flow to process the subject data.

In some embodiments, the subset of the subject data identifies multiple conditions relating to the subject. For example, the multiple conditions can identify a first condition that the events are selected to alleviate with other condition(s) that can modify the events capable of being performed to the subject. For example, if a surgical procedure can be used to alleviate a condition, the subject can include another condition that may make a surgical procedure impractical. In this example, the event to alleviate the condition can include a less invasive event, such as physical therapy.

At block 504, the method can include identifying a first processing flow that corresponds with a subset of the subject data relating to the subject. The first processing flow can one of multiple sets of queries that can be processed using the subject data.

At block 506, the method can include processing the first processing flow using the subset of the subject data to identify a series of events corresponding with the first processing flow. The first processing flow can include a series of queries in a decision tree that, when applying the subset of the subject data to each query, identifies a subsequent query in the decision tree to apply to the subset of the subject data and add at least one event to the series of events. The series of events can include events that are approved to be performed to the subject.

At block 508, the method can include updating the interface to display the series of events corresponding with the first processing flow. The interface can identify the series of events that are allowed based on the subject data. In some embodiments, the series of events includes an event chain comprising multiple related events to be provided to the subject in a specified order.

At block 510, the method can include detecting a selection of a first event to be performed to the subject. This can include obtaining a request to approve an event to be performed to the subject based on the condition relating to the subject, for example.

At block 512, the method can include displaying an acceptance message on the interface identifying the first event as an accepted event to be performed to the subject. This can be performed responsive to determining that the first event is included in the series of events. In other words, if the requested event is included in the series of events that are approved based on the processing flow, the requested event is approved and an approval message can be provided. In some instances, if the requested event is not included in the series of events, a rejection message can be provided indicating that the requested event is rejected. The rejection message may further include an indication as to which event(s) would be accepted for the subject (e.g., by identifying an event in a default event series that pertains to the subset of subject data).

It will be appreciated that variations of method 500 are contemplated. For example, block 906 (at which the first processing flow is processed using the subset of subject data) may further include accessing and processing data corresponding to a provider entity (e.g., that selects the first event at block 910). The provider entity may be identified based on (for example) login credentials that were provided prior to the selection, an IP address of a device from which the selection was received, a user selection of a provider entity, etc.

The data corresponding to the provider entity can indicate—for a given condition, test result, subject demographic and/or time period—how frequently or how often the provider performs an action corresponding to a given event (e.g., absolutely or relative to one or more other events), a health state of a subject (e.g., absolutely, relative to a given population defined based on corresponding health data and/or demographics, and/or relative to a given population evaluated by a same provider where the given population may be a total population or one defined based on corresponding health data and/or demographics). For example, the data corresponding to the provider entity may indicate how frequently the provider entity orders an imaging test responsive to a back-pain symptom relative to ordering pain injections. As another example, the data corresponding to the provider entity may indicate how frequently the provider entity prescribes opioids following a surgery relative to prescribing a non-opioid pain medication. As yet another example, the data corresponding to the provider entity may indicate a relative risk adjustment (e.g., generated based on data corresponding to the provider entity and/or one or more other entities) that indicates a risk of a subject corresponding to a given observed state (e.g., a state of health, a disease stage, co-occurrences, etc.), treatment option, etc. in view of one or more other subjects corresponding to the given observed state, treatment option, etc. or in view of another potential treatment option.

In some instances, the data corresponding to the provider entity can be evaluated in view of data corresponding to one or more provider entities (e.g., in view of a subject's given condition, in view of a subjects history), etc.). For example, it may be determined that a given provider entity is statistically more likely to prescribe a riskier or more expensive treatment corresponding to a condition (e.g., or particular stage or particular circumstance of the condition) that other provider entities; that a given provider entity is statistically more likely to depart from an event chain than other provider entities (e.g., pertaining to a particular stage or particular circumstance of the condition); and/or that a given provider entity is statistically more likely to request approvals for events in one event chain corresponding to a given condition relative to events in another event chain corresponding to the same given condition (e.g., as compared to a similar ratio associated with other provider entities, which may be generated based on a constrained subject group that may be experiencing a given condition, may be experiencing a given stage of condition, may be receiving a given treatment, may have previously received a a given treatment, etc.). The data corresponding to the provider entity (and potentially corresponding to the other provider entities) may then be used to determine whether the first event selected at block 910 is approved. For example, if a selected first event corresponds to a departure from a default event series for a given condition, a likelihood that the first event will be approved may be inversely correlated with how frequently the provider entity requests approval for events departing from default event series (e.g., in an absolute sense or relative to other entities). As another example, if a selected first event corresponds to a departure from a default event series for a given condition, a likelihood that the first event will be approved may be positively correlated with how frequently the provider entity's past performance of actions corresponding to events departing from a default event series led to positive outcomes (e.g., as an absolute measure, relative to performing actions corresponding to events in the default event series, or relative to actions performed for a same or similar condition by other provider entities).

In addition to or instead of using data corresponding to the provider entity that indicates practice patterns, data corresponding to the provider entity may include (for example) a number of years that the provider entity has been practicing, a number of subjects the provider entity has treated subjects with a given condition, a percentage of times that requests for event approvals (e.g., corresponding to a given type of event, a given type of condition, to any type of event, or to any type of condition) have been approved, etc. For example, a highly experienced specialist may be more likely to see subjects experiencing complex circumstances where normal event sequences may be inadequate to respond to a given condition. Thus, the provider entity's years of experience, specialty credentials, and/or affiliations (e.g., with a specialty team or hospital) may result in it being more likely that an event that corresponds to a departure from a default event series is approved relative to a similar request from another provider with less experience, lacking the specialty credential(s). and/or lacking the affiliation(s). In some instances, a machine-learning model (e.g., a regression model, clustering model, decision-tree model, random-forest model, etc.) may be used to predict a likelihood that a requested departure from a default event chain is likely to lead to a positive subject outcome (e.g., survival, shortened hospital stay, shortened time with a condition, shortened time being on medication, shortened time with a given symptom, etc.) relative to conforming with the default event series. A decision as to whether the first event is accepted may be made based on the prediction.

IV. Computing Environment

Figure 6:
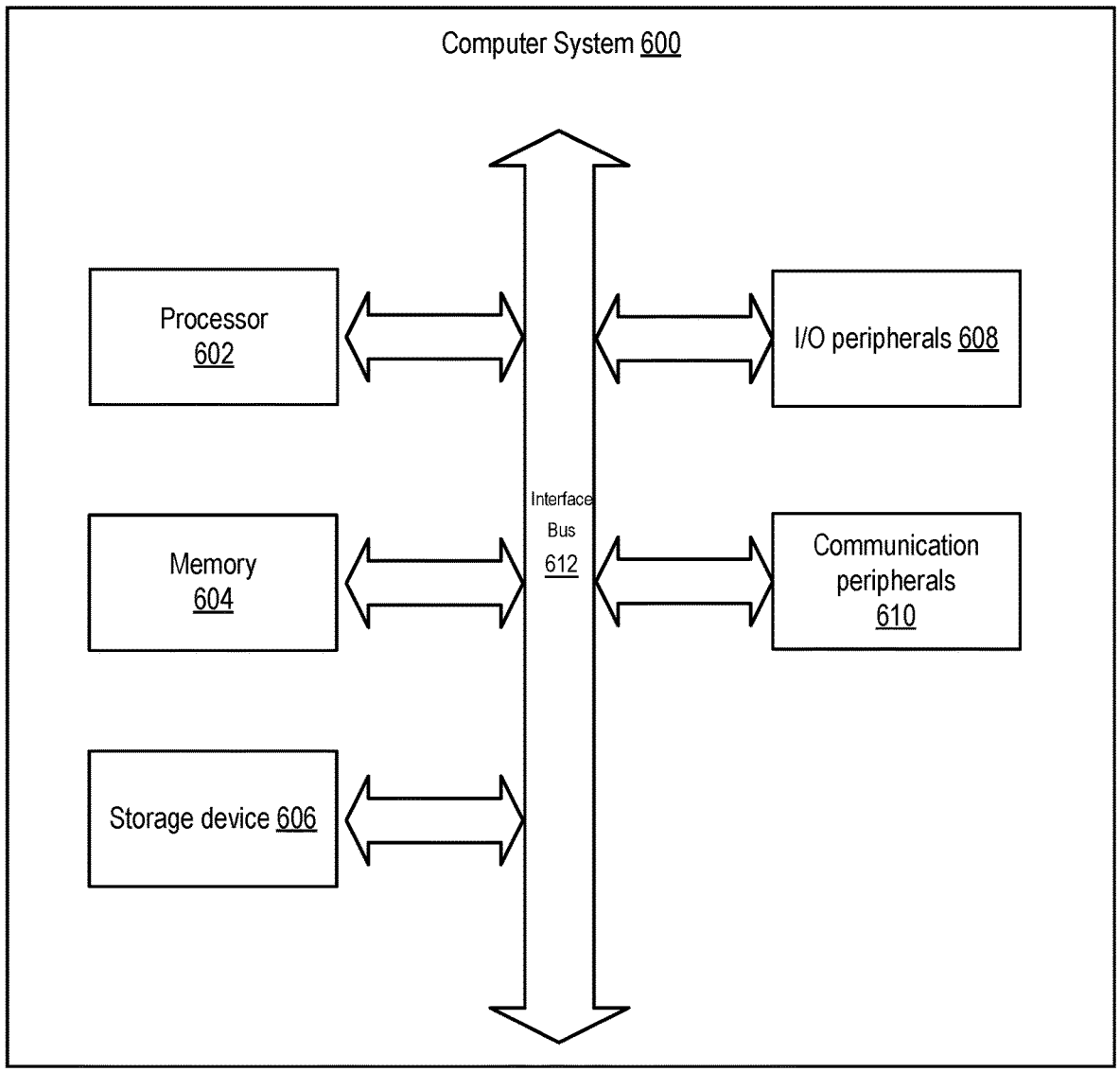
FIG. 6 illustrates an example of a computer system for implementing some of the embodiments disclosed herein.

FIG. 6 illustrates an example of a computer system 600 for implementing some of the embodiments disclosed herein. Computer system 600 may have a distributed architecture, where some of the components (e.g., memory and processor) are part of an end user device and some other similar components (e.g., memory and processor) are part of a computer server. Computer system 600 includes at least a processor 602, a memory 604, a storage device 606, input/output (I/O) peripherals 608, communication peripherals 610, and an interface bus 612. Interface bus 612 is configured to communicate, transmit, and transfer data, controls, and commands among the various components of computer system 600. Processor 602 may include one or more processing units, such as CPUs, GPUs, TPUs, systolic arrays, or SIMD processors. Memory 604 and storage device 606 include computer-readable storage media, such as RAM, ROM, electrically erasable programmable read-only memory (EEPROM), hard drives, CD-ROMs, optical storage devices, magnetic storage devices, electronic non-volatile computer storage, for example, Flash® memory, and other tangible storage media. Any of such computer-readable storage media can be configured to store instructions or program codes embodying aspects of the disclosure. Memory 604 and storage device 606 also include computer-readable signal media. A computer-readable signal medium includes a propagated data signal with computer-readable program code embodied therein. Such a propagated signal takes any of a variety of forms including, but not limited to, electromagnetic, optical, or any combination thereof. A computer-readable signal medium includes any computer-readable medium that is not a computer-readable storage medium and that can communicate, propagate, or transport a program for use in connection with computer system 600.

Further, memory 604 includes an operating system, programs, and applications. Processor 602 is configured to execute the stored instructions and includes, for example, a logical processing unit, a microprocessor, a digital signal processor, and other processors. Memory 604 and/or processor 602 can be virtualized and can be hosted within another computing system of, for example, a cloud network or a data center. I/O peripherals 608 include user interfaces, such as a keyboard, screen (e.g., a touch screen), microphone, speaker, other input/output devices, and computing components, such as graphical processing units, serial ports, parallel ports, universal serial buses, and other input/output peripherals. I/O peripherals 608 are connected to processor 602 through any of the ports coupled to interface bus 612. Communication peripherals 610 are configured to facilitate communication between computer system 600 and other computing devices over a communications network and include, for example, a network interface controller, modem, wireless and wired interface cards, antenna, and other communication peripherals.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

What is claimed is:

1. A method comprising:
   identifying a baseline event chain for a condition, wherein a baseline approval criterion is configured to be satisfied when an identified event is one of a set of events in the baseline event chain and when prior identified events are other prior events in the baseline event chain;
   identifying a set of subjects, wherein each of the set of subjects is associated with subject data that indicates that the subject is predicted to have the condition;
   tracking, for each subject of the set of subjects, each event representing a treatment provided to, an observation performed of, or a procedure performed on the subject;
   generating, for each subject of the set of subjects, an event chain based on the tracked events; detecting a subset of the set of subjects for which a particular departure between the event chains associated with subjects in the subset and the baseline event chain is observed;
   defining a series of common elements between the baseline event chain and the event chains associated with the subjects in the subset of the set of subjects;
   identifying a common set of events derived from the event chains associated with the subjects in the subset of the set of subjects based on the series of common elements, the common set of events including at least events in the particular departure;
   identifying a unique event chain including the common set of events;
   obtaining a request for approval of a first event associated with a particular subject, the request for approval corresponding to a request for approving an insurance payment request for the first event; and
   responsive to determining that the first event corresponds to any event in the baseline event chain or the unique event chain and determining that a received timestamp of the first event relative to at least one other event in an event chain that includes the first event corresponds to a timestamp of the event included in the baseline event chain or the unique event chain, providing an acceptance message on an interface executing on a computing device indicating an approval of the first event;

wherein the method further comprises:
identifying a provider entity associated with the request;
retrieving data corresponding to the provider entity; and
providing the acceptance message responsive to determining, based on the first event, the received timestamp for the first event, and the data, the approval of the first event.

2. The method of claim 1, further comprising:
generating a dataset indicative of a first result of a performance of the baseline event chain to the set of subjects and a second result of a performance of the unique event chain to the subset of the set of subjects; and
processing the dataset to derive the series of common elements for the subset of the set of subjects.

3. The method of claim 1, wherein the series of common elements comprises a number of events that relate to a number of the subset of the set of subjects.

4. The method of claim 1, wherein determining that the first event corresponds to any event in the baseline event chain or the unique event chain includes:
matching a received event code associated with the first event with an event code of the event included in the baseline event chain or the unique event chain.

5. The method of claim 1, further comprising:
responsive to determining that the first event and the received timestamp for the first event does not correspond to any event in the baseline event chain or the unique event chain, providing a rejection message indicating a rejection of the first event.

6. The method of claim 5, wherein the rejection message includes a recommendation of an event that corresponds with the baseline event chain or the unique event chain.

7. A system comprising:
one or more data processors; and
a non-transitory computer readable storage medium containing instructions which, when executed on the one or more data processors, cause the one or more data processors to perform a set of actions comprising:
identifying a baseline event chain for a condition, wherein a baseline approval criterion is configured to be satisfied when an identified event is one of a set of events in the baseline event chain and when prior identified events are other prior events in the baseline event chain;
identifying a set of subjects, wherein each of the set of subjects is associated with subject data that indicates that the subject is predicted to have the condition;
tracking, for each subject of the set of subjects, each event representing a treatment provided to, an observation performed of, or a procedure performed on the subject;
generating, for each subject of the set of subjects, an event chain based on the tracked events;
detecting a subset of the set of subjects for which a particular departure between the event chains associated with subjects in the subset and the baseline event chain is observed;
defining a series of common elements between the baseline event chain and the event chains associated with the subjects in the subset of the set of subjects;
identifying a common set of events derived from the event chains associated with the subjects in the subset of the set of subjects based on the series of common elements, the common set of events including at least events in the particular departure;
identifying a unique event chain including the common set of events;
obtaining a request for approval of a first event associated with a particular subject, the request for approval corresponding to a request for approving an insurance payment request for the first event; and
responsive to determining that the first event corresponds to any event in the baseline event chain or the unique event chain and determining that a received timestamp of the first event relative to at least one other event in an event chain that includes the first event corresponds to a timestamp of the event included in the baseline event chain or the unique event chain, providing an acceptance message on an interface executing on a computing device indicating an approval of the first event;

wherein the set of actions further comprises:
identifying a provider entity associated with the request;
retrieving data corresponding to the provider entity; and
providing the acceptance message responsive to determining, based on the first event, the received timestamp for the first event, and the data, the approval of the first event.

8. The system of claim 7, wherein the set of actions further comprises:
generating a dataset indicative of a first result of a performance of the baseline event chain to the set of subjects and a second result of a performance of the unique event chain to the subset of the set of subjects; and
processing the dataset to derive the series of common elements for the subset of the set of subjects.

9. The system of claim 7, wherein the series of common elements comprises a number of events that relate to a number of the subset of the set of subjects.

10. The system of claim 7, wherein determining that the first event corresponds to any event in the baseline event chain or the unique event chain includes:
matching a received event code associated with the first event with an event code of the event included in the baseline event chain or the unique event chain.

11. The system of claim 7, wherein the set of actions further comprises: responsive to determining that the first event and the received timestamp for the first event does not correspond to any event in the baseline event chain or the unique event chain, providing a rejection message indicating a rejection of the first event.

12. The system of claim 11, wherein the rejection message includes a recommendation of an event that corresponds with the baseline event chain or the unique event chain.

13. A computer-program product tangibly embodied in a non-transitory machine-readable storage medium, including instructions configured to cause one or more data processors to perform a set of actions including:
identifying a baseline event chain for a condition, wherein a baseline approval criterion is configured to be satisfied when an identified event is one of a set of events in the baseline event chain and when prior identified events are other prior events in the baseline event chain;

identifying a set of subjects, wherein each of the set of subjects is associated with subject data that indicates that the subject is predicted to have the condition;

tracking, for each subject of the set of subjects, each event representing a treatment provided to, an observation performed of, or a procedure performed on the subject;

generating, for each subject of the set of subjects, an event chain based on the tracked events;

detecting a subset of the set of subjects for which a particular departure between the event chains associated with subjects in the subset and the baseline event chain is observed;

defining a series of common elements between the baseline event chain and the event chains associated with the subjects in the subset of the set of subjects;

identifying a common set of events derived from the event chains associated with the subjects in the subset of the set of subjects based on the series of common elements, the common set of events including at least events in the particular departure;

identifying a unique event chain including the common set of events;

obtaining a request for approval of a first event associated with a particular subject, the request for approval corresponding to a request for approving an insurance payment request for the first event; and responsive to determining that the first event corresponds to any event in the baseline event chain or the unique event chain and determining that a received timestamp of the first event relative to at least one other event in an event chain that includes the first event corresponds to a timestamp of the event included in the baseline event chain or the unique event chain, providing an acceptance message on an interface executing on a computing device indicating an approval of the first event;

wherein the set of actions further comprises:
identifying a provider entity associated with the request;
retrieving data corresponding to the provider entity; and
providing the acceptance message responsive to determining, based on the first event, the received timestamp for the first event, and the data, the approval of the first event.

14. The computer-program product of claim 13, wherein the set of actions further comprises:
generating a dataset indicative of a first result of a performance of the baseline event chain to the set of subjects and a second result of a performance of the unique event chain to the subset of the set of subjects; and
processing the dataset to derive the series of common elements for the subset of the set of subjects.

15. The computer-program product of claim 13, wherein the series of common element comprises a number of events that relate to a number of the subset of the set of subjects.

16. The computer-program product of claim 13, wherein determining that the first event corresponds to any event in the baseline event chain or the unique event chain includes:
matching a received event code associated with the first event with an event code of the event included in the baseline event chain or the unique event chain.

17. The computer-program product of claim 13, wherein the set of actions further comprises:
responsive to determining that the first event and the received timestamp for the first event does not correspond to any event in the baseline event chain or the unique event chain, providing a rejection message indicating a rejection of the first event.

18. The computer-program product of claim 17, wherein the rejection message includes a recommendation of an event that corresponds with the baseline event chain or the unique event chain.

* * * * *